(12) United States Patent
Fine (10) Patent No.: US 9,910,254 B2
(45) Date of Patent: Mar. 6, 2018

(54) DOSIMETERS INCLUDING LENSLESS IMAGING SYSTEMS

(71) Applicant: Alentic Microscience Inc., Nova Scotia (CA)

(72) Inventor: Alan Marc Fine, Nova Scotia (CA)

(73) Assignee: Alentic Microscience Inc., Halifax, Nova Scotia (CA)

( * ) Notice: Subject to any disclaimer, the term of this patent is extended or adjusted under 35 U.S.C. 154(b) by 408 days.

(21) Appl. No.: 14/572,164

(22) Filed: Dec. 16, 2014

(65) Prior Publication Data

US 2016/0356999 A1 Dec. 8, 2016

Related U.S. Application Data

(60) Provisional application No. 61/917,195, filed on Dec. 17, 2013.

(51) Int. Cl.
*G02B 21/00* (2006.01)
*G01N 15/14* (2006.01)
(Continued)

(52) U.S. Cl.
CPC ..... *G02B 21/0008* (2013.01); *G01N 15/1429* (2013.01); *G01N 15/1434* (2013.01);
(Continued)

(58) Field of Classification Search
CPC ....... G01N 2015/1006; G01N 15/1463; G01N 15/1434; G01N 15/1475;
(Continued)

(56) References Cited

U.S. PATENT DOCUMENTS 6,083,763 A * 7/2000 Balch ................... B01J 19/0046
422/105
2006/0091289 A1* 5/2006 Cooper .................. H04N 5/262
250/208.1
(Continued)

FOREIGN PATENT DOCUMENTS

CN 106030343 A 10/2016
EP 3084473 10/2016
(Continued)

OTHER PUBLICATIONS

Aisbury, et al., "Review of retrospective dosimetry techniques for external ionizing radiation exposure," Radiat. Prot. Dosimetry, vol. 147, iss. 4, pp. 573-592, Dec. 23, 2010.
(Continued)

*Primary Examiner* — Jennifer Wecker
(74) *Attorney, Agent, or Firm* — Fish & Richardson P.C.

(57) ABSTRACT

Among other things, a method comprises imaging a sample displaced between a sensor surface and a surface of a microscopy sample chamber to produce an image of at least a part of the sample. The image is produced using lensless optical microscopy, and the sample contains at least blood from a subject. The method also comprises automatically differentiating cells of different types in the image, generating a count of one or more cell types based on the automatic differentiation, and deriving a radiation dose the subject has absorbed based on the count.

37 Claims, 6 Drawing Sheets

(51) Int. Cl.
| | |
|---|---|
| *G01N 15/00* | (2006.01) |
| *G02B 21/36* | (2006.01) |
| *G06K 9/00* | (2006.01) |
| *G01N 33/80* | (2006.01) |
| *G01T 1/02* | (2006.01) |
| *G01N 15/10* | (2006.01) |
| *G06T 7/00* | (2017.01) |
| *G01B 9/02* | (2006.01) |
| *G03H 1/04* | (2006.01) |
| *G01N 11/00* | (2006.01) |
| *G03H 1/00* | (2006.01) |
| *C12M 1/34* | (2006.01) |

(52) U.S. Cl.
CPC ..... *G01N 15/1463* (2013.01); *G01N 15/1475* (2013.01); *G01N 33/80* (2013.01); *G01T 1/02* (2013.01); *G02B 21/0004* (2013.01); *G02B 21/361* (2013.01); *G02B 21/365* (2013.01); *G06K 9/00127* (2013.01); *G06K 9/00147* (2013.01); *C12M 41/36* (2013.01); *G01B 9/02041* (2013.01); *G01N 2011/008* (2013.01); *G01N 2015/0069* (2013.01); *G01N 2015/1006* (2013.01); *G01N 2015/149* (2013.01); *G01N 2015/1486* (2013.01); *G02B 21/00* (2013.01); *G03H 2001/005* (2013.01); *G03H 2001/045* (2013.01); *G06T 7/0012* (2013.01); *G06T 2207/10056* (2013.01); *G06T 2207/30242* (2013.01); *Y10S 435/808* (2013.01)

(58) Field of Classification Search
CPC ..... G01N 2015/1486; G01N 2011/008; G01N 2015/149; G01N 33/80; G03H 2001/005; G03H 2001/045; G02B 21/0008; G02B 21/0004; G02B 21/365; G02B 21/00; G02B 21/361; G06K 9/00127; G01B 9/02041; G06T 2207/10056; G06T 2207/30242; G06T 7/0012; Y10S 435/808
See application file for complete search history.

(56) References Cited

U.S. PATENT DOCUMENTS

| | | | | |
|---|---|---|---|---|
| 2008/0176755 | A1* | 7/2008 | Amundson | B01L 3/5027 506/7 |
| 2011/0249109 | A1* | 10/2011 | Fine | G01N 21/6408 348/79 |
| 2012/0218379 | A1* | 8/2012 | Ozcan | G01N 15/1475 348/40 |
| 2013/0273524 | A1* | 10/2013 | Ehrenkranz | G01N 21/17 435/5 |
| 2013/0317369 | A1* | 11/2013 | Bryant-Greenwood | A61B 5/0059 600/476 |
| 2014/0152801 | A1* | 6/2014 | Fine | H04N 7/18 348/79 |
| 2014/0170690 | A1* | 6/2014 | Ziegler | G01N 23/00 435/29 |
| 2014/0273075 | A1* | 9/2014 | Kolanko | G01N 33/5091 435/39 |
| 2014/0300696 | A1* | 10/2014 | Ozcan | G03H 1/0443 348/40 |
| 2014/0315240 | A1* | 10/2014 | Dayel | G01N 33/491 435/29 |
| 2017/0285059 | A1 | 10/2017 | Fine | |

FOREIGN PATENT DOCUMENTS

| | | |
|---|---|---|
| HK | 1227111 | 10/2017 |
| WO | WO2015/089632 | 6/2015 |

OTHER PUBLICATIONS

International Preliminary Report on Patentability from corresponding PCT application PCT/CA2014/000891 dated Jun. 30, 2016 (7 pages).

International Search Report and Written Opinion from corresponding PCT application PCT/CA2014/000891 dated Mar. 17, 2015 (8 pages).

Seo, Sungkyu et al., "High-Throughout Lens-Free Blood Analysis on a Chip," Analytical Chemistry, vol. 82, No. 11, pp. 4321-4627, XP055245029, US ISSN: 0003-2700, DOI: 10.1021/ac1007915, May 7, 2010 (7 pages).

European Search Report from corresponding European application No. 14870804.3 dated Jul. 24, 2017 (5 pages).

* cited by examiner

DOSIMETERS INCLUDING LENSLESS IMAGING SYSTEMS

This application is entitled to the benefit of the priority of the filing date of U.S. provisional patent application 61/917,195, filed Dec. 17, 2013. This application is also related to U.S. patent application Ser. No. 61/255,781, filed Oct. 28, 2009; Ser. No. 12/913,639, filed Oct. 27, 2010; Ser. No. 13/095,175, filed Apr. 27, 2011; 61/761,467, filed Feb. 6, 2013; 61/785,762, filed Mar. 14, 2013, and 61/839,735, filed Jun. 26, 2013. All of the applications named in the prior sentence are incorporated here by reference in their entireties This disclosure relates to dosimeters including lensless imaging systems, and methods and systems associated with the dosimeters.

In some approaches, biological responses to radiation dose, or biodosimetry, are measured by analyzing chromosome abnormalities, such as dicentrics and ring forms in peripheral blood lymphocytes. Alternatively or in addition, the measurement can also be performed by detecting radiation-induced free radicals in tooth enamel, e.g., using electron paramagnetic resonance.

In other approaches, biodosimetry is performed by monitoring dose-dependent, radiation-induced lymphopenia, neutropenia, leukopenia, thrombocytopenia and/or pancytopenia that develop over hours or days after radiation exposure. Typically, the monitoring is performed by skilled technicians using complex instrumentation. In some situations, flow cytometers and microscopes can be used for associated hematological analyses.

SUMMARY

In general, in an aspect, a method comprises imaging a sample displaced between a sensor surface and a surface of a microscopy sample chamber to produce an image of at least a part of the sample. The image is produced using lensless optical microscopy, and the sample contains at least blood from a subject. The method also comprises automatically differentiating cells of different types in the image, generating a count of one or more cell types based on the automatic differentiation, and deriving a radiation dose the subject has absorbed based on the count.

In general, in another aspect, an apparatus comprises a lensless imaging system and a processor. The lensless imaging system comprises an array of sensors having a common sensor surface and a microscopy sample chamber. The chamber comprises an upper surface. A space between the upper surface and the sensor surface is to receive a sample for imaging. The processor is configured to automatically receive an image of at least a part of the sample generated by the lensless imaging system. The sample contains at least blood from a subject. The processor is also configured to automatically display information associated with radiation dose absorbed by the subject.

Implementations of the methods and/or apparatuses may include one or any combination of two or more of the following features. Generating a count of one or more cell types comprises generating a count of lymphocytes. Lymphocyte depletion is estimated based on the count of lymphocytes. The sample is a first sample taken at a first time from the subject and count for lymphocyte is a first count for lymphocyte, and a second sample taken at a second, different time from the subject is imaged, a second count of lymphocyte is generated based on the second sample, and lymphocyte depletion based on the first and second counts of lymphocyte is estimated. The sample contains fiduciary beads distributed among blood cells of the sample. The cells of different types are differentiated based on one or more of color, size of cell, nuclear shape, and nuclear size. The count of one or more cell types is generated with correction for a volume of the imaged sample. The sample contains diluted blood from the subject, and the count of one or more cell types is generated with correction for dilution of the blood. The sample contains one or more of anticoagulant, diluent, stain, antibody, erythrocyte lysing solution, and other reagents. Generating a count of one or more cell types comprises generating the count based on detection one or more surface antigens associated with the one or more cell types. The imaging is performed without using a lens. The imaging comprises imaging at a resolution of 1 mega pixels or higher. The imaging comprises rapid remixing and resampling the displaced sample by raising and lowering the surface of a microscopy sample chamber. The image contains information about cells distributed in no more than a monolayer layer in the sample. The array of sensors is formed in a CMOS chip. Each sensor of the array of sensors has a size of about 2 µm by 2 µm or smaller. The processor is configured to automatically analyze data contained in the image. Automatically analyzing the data comprises classifying different types of cells in the image. The processor is configured to generate a count of one or more cell types. The processor is configured to derive the radiation dose the subject has absorbed based on the count. The processor is configured to automatically deliver the received image to a machine external to the apparatus for the machine to process information contained in the image and provide information about the radiation dosage. There is a network interface for connecting the apparatus to a network through wire or wireless connections. The apparatus is a handheld device. The sensors comprise digital image sensors capable of lensless optical microscopy.

Implementations may provide one or more of the following advantages. Dosimeters, including lensless imaging systems can provide rapid, point-of-care determination of radiation doses absorbed by subjects after radiation exposure. The devices can be operated by a patient for self-assessment or in the field by unskilled operators without special training. The dosimeters are compact in size and are portable, e.g., in pockets. They are made at a low cost, permitting wide and quick deployment, e.g., for fast triage of large populations. The dosimeters implement platform optical microscopy technology and are suitable for additional capabilities, such as counting of any type of normal blood cell, detection of abnormal blood cells or parasites, and chemical analysis of blood or other fluids. Modifications to or services of the devices can be readily performed, even in the field. The samples for use with the dosimeters can be readily prepared, e.g., collected from a finger of the patient and prepared using a pipette with pre-loaded materials, and transferred to the dosimeter at a high rate, e.g., at less than one minute per sample. The throughput of the dosimeter use can be high, e.g., 30 tests or more per hour.

Other features, objects, and advantages of the invention will be apparent from the description and drawings, and from the claims.

The figures and elements shown in them are not always to scale and many of them are illustrated schematically. The spatial relationships of the elements in the figure may appear differently than the descriptions in the text, for example, above and below and top and bottom may be shown oppositely in the figures from the way they are described in the text.

DETAILED DESCRIPTION

Overview

Accidents involving a nuclear reactor or transportation of radioactive materials, as well as terrorist actions, could expose a large population to hazardous, potentially lethal, radiation. In such events, it would be desirable to determine quickly which individuals in that population require urgent medical treatment. To conduct a triage for a large population, e.g., many tens or hundreds of thousands, or even of millions of people, the radiation dose absorbed by each individual needs to be estimated rapidly and efficiently, using a device having a high throughput, possibly even by untrained operators. One possible way to achieve the estimation, at least in part, is through biodosimetry, i.e., measuring biomarkers in accessible tissues of individuals, the levels of which have a quantitative relation to the absorbed radiation doses. Examples of such biomarkers include radiation-induced free radicals in tooth enamel, which can be measured by electron paramagnetic resonance (EPR), onset of clinical signs such as vomiting, incidence of chromosome abnormalities or histone phosphorylation in peripheral blood leukocytes, and changes in absolute count of various cell types in peripheral blood.

Among the radiation biomarkers, depletion of lymphocytes is highly correlated with chromosome abnormalities and tooth enamel EPR, and is a reliable radiation biomarker. The depletion of lymphocytes in peripheral blood can be measured robustly and reliably for radiation dose estimation.

A dosimeter of this disclosure counts lymphocytes in peripheral blood and provides rapid, early, and accurate triage for a large population. The dosimeter can be compact and portable, e.g., handheld. For example, the dimensions of the dosimeter are about 20 cm×12 cm×5 cm. The dosimeter is easy to use and provides reliable results in a short period of time, e.g., minutes. In some examples, the dosimeter automatically counts lymphocytes and total white blood cells from a finger prick of whole blood at the point of care, and outputs the counts and/or a screen result, e.g., an indication of whether or not the individual being measured needs to be treated, in 2 minutes or less. The dosimeter can send an indication to an operator when the dosimeter determines based on the measurement that the person being measured has been exposed to radiation exceeding a predetermined threshold, e.g., 2 Grey (Gy) or more. The indication can contain detailed cell counts and/or radiation dosage information. However, in some situations, the indication can be as simple as whether or not the person being measured needs further medical care. The indication can have various forms, e.g., visual or audio. As a result, the dosimeter can be used by health care professionals or by untrained persons. The dosimeter can also be relatively inexpensive so that a large number of them can be distributed to increase the speed of population triage. In emergency radiation exposure situations, there is also the likelihood that a significant number of unexposed individuals are presented to the triage site, demonstrating similar symptomology. Multiple, e.g., hundreds of, thousands of, or even more, dosimeters can be distributed in the field to professionals and/or non-professional local responders to carry out high-throughput triage. Individuals who need treatment due to the radiation exposure can be identified within a brief therapeutic window for effective treatment. Sometimes the individuals are equipped with the dosimeter and can conduct self-assessment.

Figure 3:
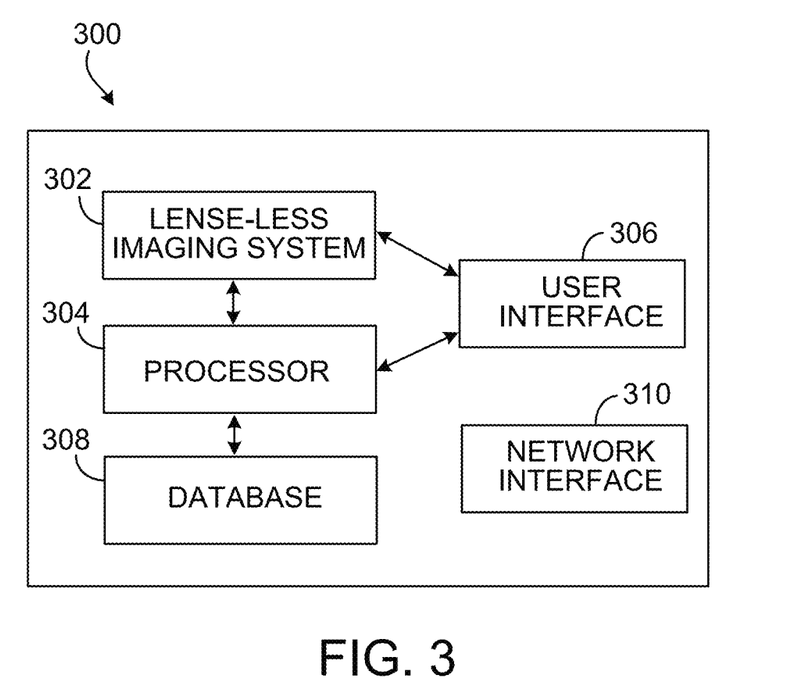
FIG. 3 is a schematic block diagram of a dosimeter.

Referring to FIG. 3, a dosimeter 300 includes a lensless imaging system 302 and a processor 304 in communication with the lensless imaging system 302. The processor 304 may execute one or more algorithms for controlling the lensless imaging system 302 and for analyzing the image, e.g., detecting and classifying cells automatically, or plotting lymphocyte depletion curves following radiation exposure based on previously published data. Optionally, the dosimeter includes a database 308 that stores the published data and other data for performing the data analysis. The result of each analysis can also be stored in the database 308 for later use, e.g., for statistical studies. In some implementations, subject identifiers for the analyses, such as name, social security number, etc. can also be stored in association with each analysis. In some implementations, the results of the analyses can also be stored in a database remote to the dosimeter, e.g., on a computer. The data can be entered into such a database directly from the dosimeter, or through a touch screen or a keypad, or by voice recording, e.g., with speech recognition software. The dosimeter 300 can include a network interface, e.g., a USB port, a wire connection, or a wireless connection, such as Internet connection, so that the dosimeter 300 can connect to a network or another machine. Data can be downloaded from and/or uploaded to the dosimeter 300. Also optionally, the dosimeter 300 includes a user interface 306, e.g., a display and an input mechanism, through which an operator interacts with the dosimeter 300.

In some implementations, alternative to or in addition to controlling the imaging system and/or analyzing data, the control and/or the data analysis can also be performed external to the dosimeter 300. For example, the dosimeter 300 can connect, e.g., wirelessly, to an external processor, e.g., a computer or a smart phone, that implements the one or more algorithms that control the lensless imaging system and/or analyze the data. The algorithms can be distributed to the external processor, e.g., through network distribution such as emails or website downloads, or through hardcopies such as CDs. The external processor can be local to the dosimeter 300, e.g., a smart phone or a tablet of an operator, so that the external processor can be connected to the dosimeter through wire or wirelessly. The external processor can also be remote to the dosimeter 300, e.g., a remote server. The remote server can be backed with one or more large databases for use in precise measurement. Using the external processor, components of the dosimeter, such as the processor 304, the database 308, and/or the user interface 306 can be simplified or even eliminated, such that the cost, weight, and/or size of the dosimeter are reduced. For example, a dosimeter that is connectable to a laptop computer using USB ports for operation can have a size of about 8 cm×5 cm×6 cm or smaller.

The lensless imaging system 302 has a digital image sensor architecture that is capable of performing massively parallel, near-field optical microscopy. An example of the digital image sensor is CMOS image sensors, the details of which are explained further below. The CMOS image sensors can be arranged in arrays. The resolution of the sensors is not limited by diffraction, but instead is determined by the size of the near-field aperture (i.e., the pixel). The CMOS sensors can have a high imaging resolution, e.g., 1.4 μm square pixels, 1.1 μm square pixels, 0.9 μm square pixels, or even higher. The system 302 does not require scanning, focusing, or other moving parts.

Figure 4:
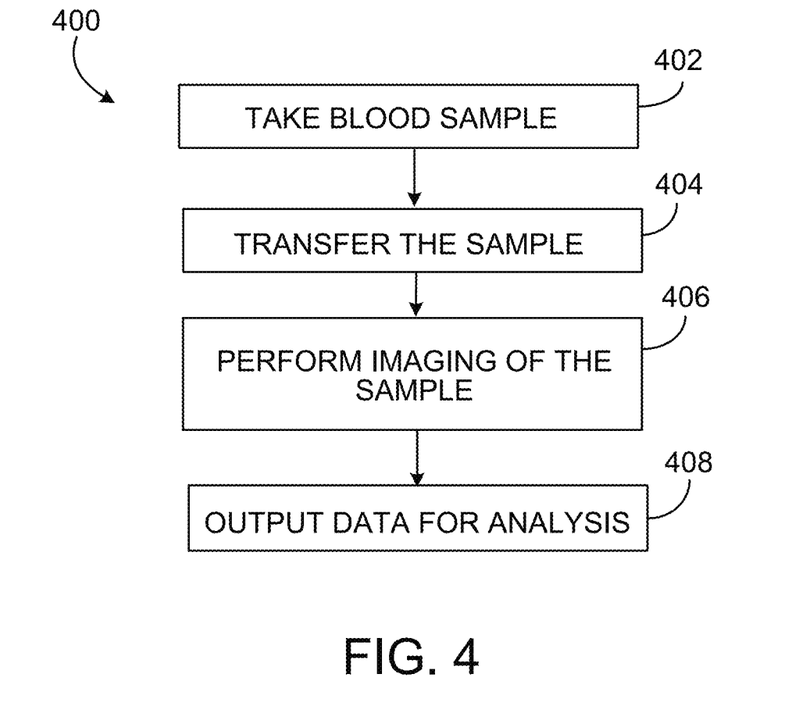
FIG. 4 is a flow diagram.

In use, a specimen, or a sample, of blood is placed close to or on the sensor surface. The lensless imaging system 302 images a monolayer of fresh blood cells with sufficient resolution to identify the most relevant cell classes over a small area, e.g., 10 mm$^2$, that contains sufficient numbers of cells for useful analysis. The samples for the analysis can be relatively small, e.g., 10 μL, 1 μL, or even less. FIG. 4 shows an example process of imaging the blood sample using the lensless imaging system. Initially, blood samples are taken (402), e.g., from a standard lancet finger prick using disposable capillary pipettes provided with the dosimeter. The pipettes are preloaded with a pre-determined amount of stain and/or other reagents so that the blood is stained when discharged from the pipettes. The sample containing the stained blood is then discharged (404) into to a sensor chamber of the dosimeter. The chamber is closed and the imaging system images (406) the sample. In some examples, individual full-field images at full resolution, e.g., 8 million pixels, can be obtained in approximately 0.05 seconds. The lensless imaging system 302 then outputs (408) data, e.g., data that represents the images, to an internal or external processor for analysis. One example of the data analysis is improving the image quality by a variety of computational means, e.g., by combining multiple sequentially obtained images according to methods known in the art, for example, as described in Milanfar P (2010) Super-Resolution Imaging (CRC Press, Boca Raton, Fla.), the entire content of which is incorporated here by reference.

Example Lensless Imaging Systems

Figure 1:
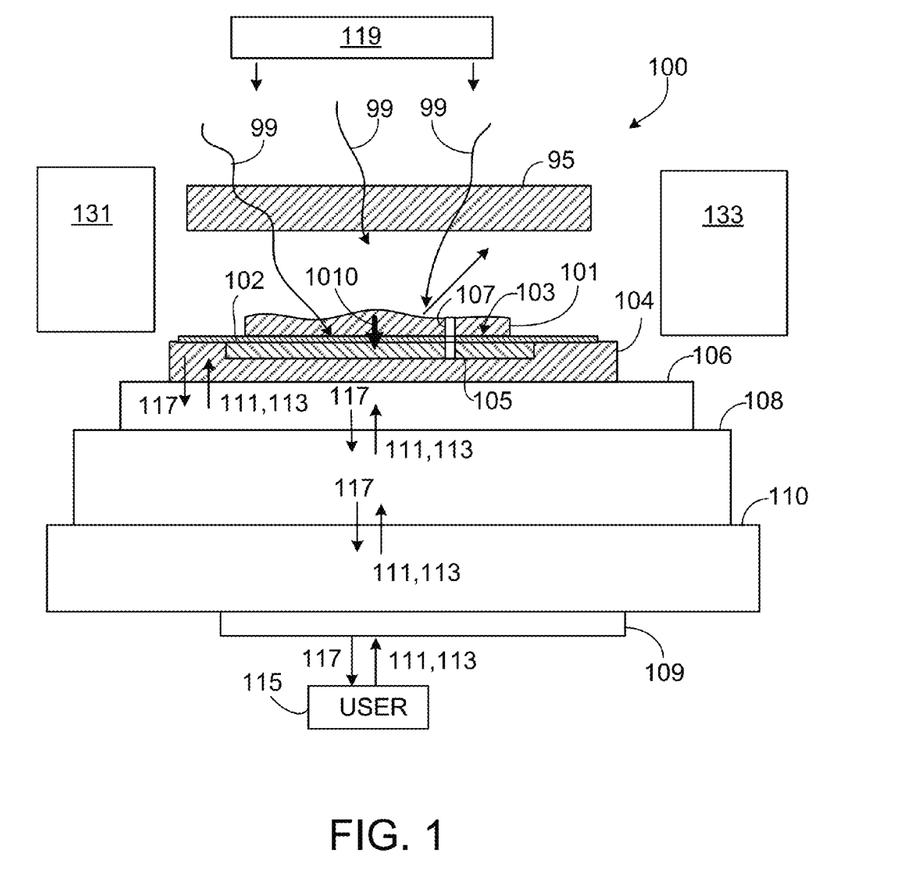
FIG. 1 is a schematic side view partly in section of a system to detect and use light representative of a sample.

As shown in FIG. 1, in some implementations of the concepts that we describe here, a system 100 can capture high resolution images (e.g., full-color, gray-scale, "black-and-white" or a combination of them) of a sample 101 (e.g., a sample in a gas phase, a liquid phase, or a solid phase, or a combination of those or other forms) that is in contact with (or in close proximity to) a light sensor 102. The light sensor includes a two-dimensional arrangement of light sensitive elements 105 that can correspond to an array of pixels in the image. We sometimes refer to the elements of the light sensor as pixels for simplicity We sometimes use the phrase "light sensitive locations" in the broadest sense to include, for example any features of a device that are separately sensitive to light or separately capable of emitting light, or both, including light sensitive elements or pixels and light source locations. We sometimes use the phrase light source locations to refer to elements capable of emitting light. In some cases we use the phrase light sensitive location to refer to an exposed light sensitive portion of a feature of the device without any covering, protective layer, shield, or any other feature that might separate the light sensitive from the ambient or from a sample.

We sometimes use the phrase "contact microscope" or "contact microscopy" to refer in the broadest sense to any device (or technique) that includes (a) a high resolution sensor of closely spaced light sensitive or a high resolution set of light emitting locations that are exposed to the ambient at a surface of the device together with (b) a device to associate with that surface a portion of a sample that is to be imaged, and, in the case of light emitting locations, a light detector relatively far from the light emitting locations and sample, so that the portion of the sample is in contact with (or nearly in contact with) the surface and a usable high resolution image can be obtained by the sensor when the portion of the sample is in place.

In contact microscopy, the sample is either in direct contact with the light sensitive features of the sensor, or light emitting features of the light source, without any intervening material, or the sample may be nearly in contact with the light sensitive or emitting features. By nearly in contact, we mean, not in direct contact. However, the closeness between the sample and the light sensitive or emitting features may vary based on one or more factors, including the type of light. For example, in some cases this may mean within the near field of the features, i.e., at a distance that is within ½ of the wavelength of the light involved or possibly at a distance that is within a wavelength of the light involved. In another example, when illuminated with collimated light, the specimen can be several micrometers away from the sensor surface while yielding good quality images. For some applications, the distance can be up to tens of micrometers while producing good quality images.

We use the concept of a device to associate the sample with the surface in its broadest sense to include any mechanism of any kind that facilitates the movement, flow, delivery, placement, or presentation, for example, of a portion of the sample into contact with or nearly into contact with the light sensitive locations, including any mechanism that uses mechanical, electrical, electromechanical, acoustic, magnetic, pneumatic, hydraulic, gravitational, inertial, or other features, for example.

Sometimes the amount of sample loaded onto the sensor is larger than the amounted needed for imaging. In some implementations, the sample needs to be in the form of a relatively thin layer, e.g., 1 μm to 100 μm, or have a thickness such that a single layer of cells of the sample is dispersed on the sensor for imaging. A lid or cover or chamber or chamber top 95 can be moved (or can descend) to contact the sample and adjust the amount of sample, e.g., the thickness of the sample, on the sensor. As an example, the adjustment can be done by pressing one end of the chamber top 95 against the sample 101 so that the excessive amount of sample flows out of the perimeters of the sensor 102. The chamber top can also descend in other manners. We sometimes refer to the space that is between the surface of the chamber top 95 that has completed its descent and the sensor surface 102 and in which the sample is located as a chamber.

The sensor can also include other components either as part of or in addition to the light sensitive elements, to drive or read the elements, generate, process, or deliver signals to and from the elements, and perform other functions. Generally, when we refer to the sensor we mean the integrated circuit or part of it that (a) receives light (or sometimes emits) at light sensitive elements and generates signals or data representing the intensities of light detected by the light sensitive elements, and (b) any electronic elements that directly drive the light sensitive elements or cause the light-generated signals or data to be delivered by the light sensitive elements, but not (c) any other circuitry used to process the signals or data to form the image.

The sensor 102 can be part of or formed on an integrated circuit chip 104, which can be made in a homogeneous fabrication mode or a hybrid fabrication mode. The chip 104 can be mounted on a headboard 106, and the headboard 106 can be part of or be connected to a control unit 108. In some applications, a lid or cover or chamber or chamber wall 95 can abut, touch, surround, enclose, or contain the sample or a portion of it within a space or chamber adjacent to an exposed surface 103 of the sensor or a portion of the headboard or both.

The control unit 108 can be part of or connected to a user device 110. The user device 110 can provide an interface 109 with a user 115; can receive commands 111 and information 113 through the user interface from the user, process them, and forward them to the control unit 108; and can receive information 117 from the control unit, process it, and provide it to the user through the user interface. In some instances, the user interface can operate through the control unit 108 or the headboard 106 or a combination of them and of the user device. And commands and information 111, 113, and 117 can be passed between any two or more of the components.

The system can also include sample transport and management devices 131, 133, that can include mechanical, electrical, or electronic components or combinations of them that enable or cause the sample to be delivered to the sensor, held at the sensor, and removed from the sensor, as needed. The devices 131, 133, can also process the sample before and after imaging including by mixing materials with the sample, removing materials from the sample, fetching the sample from a source, disposing of the imaged sample, and any other function that may be needed with respect to the sample in order to operate the system to perform the imaging.

The user device 110 can be a smart phone, another kind of handheld device, an instrument, a system, a manufacturing component, a work station, or any other user device including one that is dedicated to the function of interacting with the control unit or one that has functions not limited to interaction with the control unit, or a combination of the two.

A complete working system or commercial product or component need not include all of the sensor, the chip, the headboard, the control unit, and the user device, but could include a combination of any two or more of them.

In various implementations, any combination of two or more of the sensor 102, the chip 104, the headboard 106, the control unit 108, and the user device 110 can have a variety of mechanical and electrical connections among them. In addition, mechanical, fluid flow, electronic, software, data processing, communication, storage, and electrical functions needed for various operations can be distributed in a variety of ways between and among pairs and three or more of those parts of the system. The distribution of functions can be arbitrary or based on commercial and technological considerations in a wide variety of ways.

In some instances, the sensor 102, which we use to refer to the light sensitive area of the chip 104, can operate as a charge-coupled device (CCD) or as a complementary metal-oxide semiconductor (CMOS) sensor. Other imaging regimes may be possible. As mentioned earlier, in some examples, the sensor is pixelated, that is, operates with respect to rows and columns (or other array arrangements) of light sensitive picture elements (pixels) 105.

During operation, the sensor responds to incident electromagnetic radiation (e.g., light) 99 that passes through 1010, is scattered from, or emanates from the sample 101. Light that passes through or is scattered from or emanates from the sample may be altered in wavelength, for example, as it passes through or is scattered or emanates. The incident electromagnetic radiation 99 and the transmitted, scattered, or emanated radiation is typically in the wavelength range of visible light, near ultraviolet, or near infrared. We use the term light in its broadest sense to include all such ranges, for example.

Because the sample 101 is in contact with or essentially in contact with or in close proximity to the surface 103 of the sensor, there may be no need for any optical elements to be used in the system to refract or collimate or redirect the light from the sample to the sensor.

Light from a portion 107 of the sample that is adjacent to a pixel (or is in a path between the incident light 99 and the pixel) will be received largely (in some cases essentially entirely) by that pixel 105.

In this arrangement, the light sensed by the array of pixels of the sensor is directly representative of a corresponding array of portions of the sample and therefore represents in effect an image of the sample, an image that can be of high resolution.

To the extent that the initial source of the light reaching the sensors is in the environment, that light may be ambient light or can be provided by a dedicated light source 119. In some implementations it may be useful to control the illumination of the sample and in particular the uniformity or orientation of the illumination by controlling the light source or screening out ambient light or both.

To capture an image of the sample, the sensor is driven and read during a conceptual image capture cycle. During an image capture cycle, the light received by the sensor at all of its pixels is converted to electrical signals (e.g., analog signals or digital values) that are delivered to electronic components of the chip. The signals may be read in parallel or serially depending on the technology. The electrical signal from each of the pixels typically is represented by a quantized intensity value corresponding to the intensity of light sensed by the pixel, within some range such as a range represented by 14-bit digital values. Color information can be obtained in a variety of ways, for example, using different band-pass optical filters systematically arrayed over adjacent pixels, or sequential imaging with different color illumination, and possibly in other ways. Whatever method is used, the electrical signals that are received from the various pixels in space and/or time together can represent a full-color high-resolution high-dynamic range image of the sample.

In addition to the electronic features of the system, there are mechanical elements discussed below that among other things handle, contain, and illuminate the sample 101.

Some or all of the electronic and mechanical components that form the system, including the sensor, the chip 104, the headboard 106, the control unit 108, the user device 110, and the user interface 109, and combinations of any two or more of them can be produced as individual commercial products and can be either reusable or disposable.

For high resolution imaging, a monolayer of each sample is imaged. The monolayer imaging can be achieved by controlling the sample volumes loaded onto the sensors. Examples of such control include sample processing before loading the sample onto the sensors, mechanical control using the chamber of the lensless imaging system 100 after the sample is loaded into the chamber, and/or the combination of both.

Figure 2:
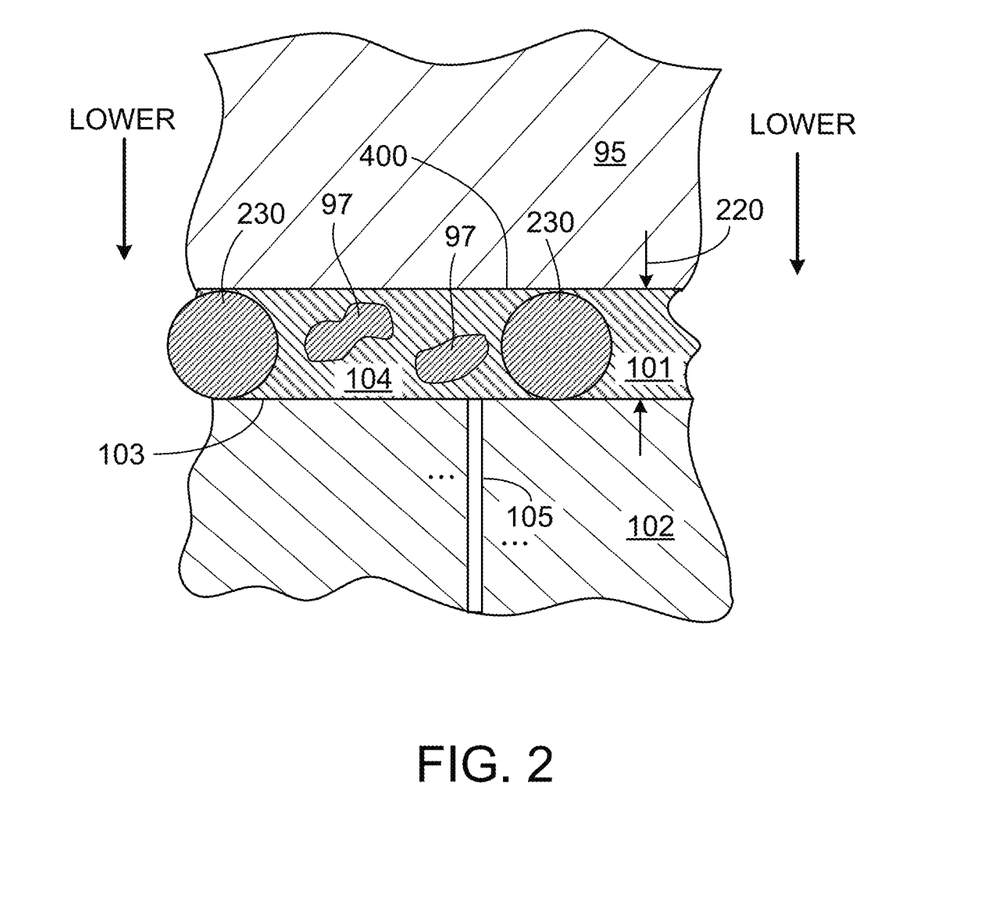
FIG. 2 is a schematic sectional side view of elements useful to detect and use light representative of a sample.

Referring to FIG. 2, the sample 101 (we sometimes use the word specimen interchangeably with the word sample) that is being imaged can be composed of or include small similar types of units 97, such as particles, bits, specks, organisms, cells, or molecules, or combinations of them or combinations of any two or more of the different types. The units 97 may be suspended in or carried in a liquid 104 to form liquid-suspended sample units 97, entrained in a gas to form gas-suspended sample units (not shown), rest in an unsuspended and un-entrained form (a powder, for example) on the surface of the sensor (not shown), or be held in an integrated matrix of solid, gelled, or other integral self-supporting material, such as a sectioned layer of tissue, to name only a few examples. We sometimes use the term matrix very broadly to include, for example, any material in which sample units are held, including liquid, gas, solid, gel, or any other material.

Additionally, the sample 101 can also contain spacing features 230 for controlling the volume of the sample 101 on the sensor 102. In some instances and for a given kind of sample unit or a precisely specified volume of sample (e.g., for a blood count, or other analysis in which the number of sample units is to be counted for a precise volume of the sample), the volume of the sample imaged by the sensor is precisely controlled by the width and length of the top active imaging surface of the sensor and by the height of the gap 220 (or the chamber) between that surface and the flat bottom surface of the chamber top. In some cases, the volume may not need to be precise, but the gap height may need to be a precise amount, or no larger than a certain amount, or no smaller than a certain amount, or a combination of those conditions.

A wide variety of techniques and devices can be used to form and maintain a height (e.g., a precise height) of the gap. We broadly refer to those techniques and devices as spacing features. In the example shown in FIG. 2, the spacing feature includes microspheres or other kinds of beads of uniform size, say, 1.0 µm or 3.0 µm or 5.0 µm. To establish a precise and uniform spacing and therefore volume of the sample space, it may be useful to specify the precision of the bead sizes, for example, the beads could be specified as 2.0 µm with a precision of plus or minus 100 nanometers. The beads can be non-spherical. The beads can be used in a variety of different ways.

As shown in FIG. 2, in some implementations, the beads 230 are included within the sample, for example a sample having a liquid matrix in which sample units (which may be smaller than the beads) are suspended, when the sample is delivered to the sensor surface 103. If the chamber top is then allowed to settle on or be pressed down onto the sample, and assuming that there are enough beads in the sample and they are reasonably well distributed within the liquid, then a uniform accurate gap height can be achieved. For this purpose, the beads might be present in the sample at a concentration of 10,000-500,000 beads per microliter of sample, for example. Maintaining an even distribution of the beads in the sample can be done by simple mechanical agitation if the beads are selected to have close to neutral buoyancy in the sample.

In some cases, the beads can be roughly the same size as the sample units. In some implementations, beads of two different sizes can be included. A larger size defines the intended spacing. A smaller size can be counted to verify that the volume of the sample space is as intended, assuming the smaller beads are distributed through the sample reasonably uniformly, and the number of smaller beads per unit volume of the sample is known. The beads may be transparent in order to allow light to pass through to the sensor, or may be colored, or fluorescent, or opaque, or a combination of two or more of those characteristics.

After a sample is loaded into the chamber, the chamber top can be lowered relative to the sensor surface 103 to remove the excessive volume of sample from the sensor 102 and allow the sample units 97 (such as cells that are disbursed in a fluid) to be evenly distributed over the surface 103 of the sensor 102. In some implementations, the removal of the excessive volume does not alter the bulk concentration of the sample units so that the imaging of a relatively small volume of the sample, e.g., about 1 µL, produces data applicable to the bulk sample, e.g., about 40 µL or more, dispensed onto the sensor. In other implementations, the new concentration is consistently proportional to the bulk concentration of the sample units, allowing for a correction factor to be determined. To achieve the desired sample concentration for imaging, the sample can be further processed as described further below.

The chamber top can be lowered in various ways. In one example, referring again to FIG. 2, the chamber top has a flat top surface 400 and during the lowering of the chamber top, the top surface 400 is kept substantially parallel to the top surface 103 of the sensor 102. We sometimes call this process a flat, linear descent.

Example Dosimeters

A dosimeter, such as the dosimeter 300 of FIG. 3, including a lensless imaging system, such as the system 100 of FIG. 1, can perform fast and reliable biodosimetry for self-assessment or by large numbers of emergency health care providers without specialized training in the technology to triage a large population within one or two days of a major radiation event. The dosimeter can be a pocket-sized device that measures absolute counts of particular white blood cells for estimating the absorbed radiation dosage via lymphocyte depletion. The dosimeter can have high sensitivity, specificity, repeatability, and reproducibility. The turnaround time for the analysis process, e.g., including at least steps 404, 406, 408 of the process 400 in FIG. 4, is a few minutes or less. The dosimeter is operable and outputs indications that are readily understandable by people without extensive training in the technical field, e.g., paramedics or other emergency care givers. A patient can even use the dosimeter to conduct self-assessment. The dosimeter can be powered by batteries or other power supplies and can be energy efficient. For example, the dosimeter can run for at least 24 hours without battery replacement or recharge. The device is reliable such that the mean time between failures is high, for example, many tens or hundreds of hours. The device can include self-diagnostic capabilities to identify components that have failed, and such components can be readily replaced in the field. An operator can interact with the dosimeter through a graphical user interface.

The dosimeter can be autonomous and be capable of computing, displaying, archiving, and wirelessly transmitting results with no external computer required for any aspect of operation. In addition, the dosimeter includes sensor control electronics, illuminator, display, and reporting components that can be addressed by electrical, mechanical, and software engineering.

The dosimeter can contain a CMOS chip that provides a sensor surface of about 8.25 mm$^2$ and includes 3280 by 2464 arrays of 1.1 µm pixel sensors, with good resolution and sampling statistics. The chip can collect sample images at video rate, e.g., about 24 full frames per second. The chip may be relatively thin, e.g., about 200 µm to about 300 µm. Although not shown or discussed with respect to FIGS. 1 and 2, the lensless imaging system of the dosimeter can detect fluorescence. For example, the image sensor surface includes one or more layers of filters, which can include UV (ultra violet)-blocking filters that are compatible with transmitted-light microscopy over visible wavelengths. Fluorescence imaging of the samples can then be performed, for example, by UV excitation. Fluorescence imaging may allow use of additional biodosimetry markers, such as levels of phosphorylation of histone gamma-H2AX in lymphocytes, which may be particularly valuable for early monitoring, e.g., less than 24 hours post-exposure, and low dosage, e.g., less than 1 Gy.

The one or more algorithms for controlling the lensless imaging system and for analyzing the data output from the lensless imaging system can be pre-developed. The algorithms may also be updated based on use of the dosimeter. In some implementations, published biodosimetry data, acute radiation syndrome literature, and internally generated data are used to determine dosimeter parameters for sample handling and data analysis e.g., for lymphocyte and other blood cell-based hematological biodosimetry. The parameters can be further analyzed and validated using existing samples to confirm that detectability and reliability of the dosimeter are adequate for triage purposes. In some implementations, the analysis and validation processes may identify potential interfering substances and conditions that could confound the interpretation of results from the dosimeter.

In addition to the dosimeter, to facilitate the blood sampling and imaging, a pipette system for sample collection, transfer, and addition of reagents, antigens and/or volume fiduciary microbeads can be provided to the dosimeter operator. Reference bead suspensions for system calibration can be taken into consideration in the algorithms that control the lensless imaging system and analyze data to improve accuracy of cell classification.

In some implementations, accuracy of cell classification can also be enhanced by immunologically detecting specific surface antigens, for example, CD3 and CD19, to detect T and B lymphocytes. Further to the sample processing discussed above, e.g., adding reagents, staining, and/or adding microbeads, before imaging, fluorescent or microbead-labeled antibodies directed against surface antigens such as CD3 and CD19 are added to a processed sample. Such an addition can render the classification of lymphocytes in the blood sample unambiguous, as the lymphocytes are rendered fluorescent or "decorated" with the microbead-coupled antibodies. The antibodies can also be included in the pipette system. However, the addition may increase the overall cost and sample handling complexity.

In use, referring again to FIG. 4, a blood sample is taken (402) by applying a standard lancet to the subject's cleaned, e.g., using disposable alcohol swab, finger tip. Sequential drops of blood are expressed according to standard practice. To transfer (404) the sample, a transfer device takes up a portion of a drop, which may be as little as 5 µl or as much as 50 µl. The transfer device may be a volumetric pipette, a calibrated capillary tube, a micropipette or other similar devices. In some implementations, the portion is a portion of a third drop of the sequential drops. Taking the measurement from the third drop may improve measurement precision. The transfer device may be preloaded with anticoagulant, diluent, stain, antibody, fiduciary beads, erythrocyte lysing solution and/or other reagents. Alternatively, one or more of these materials may be added to the blood sample by one or more other pipettes, in predetermined volume(s) proportion to the volume of blood. The blood, diluted with such reagents or not, is transferred to the chamber of the lensless imaging system, and is illuminated and imaged (406). The volume of the imaged blood is determined by prior calibration of the chamber dimensions, by inclusion and counting of fiduciary beads added to the blood at a known concentration, and/or by other means.

Figure 5A:
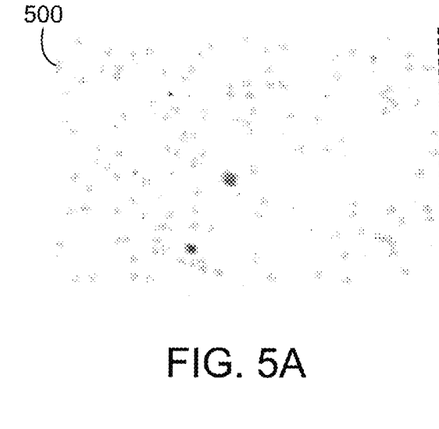
FIG. 5A is an enlarged view of a portion of an image field of a blood sample before the cells in the sample are classified.
Figure 5B:
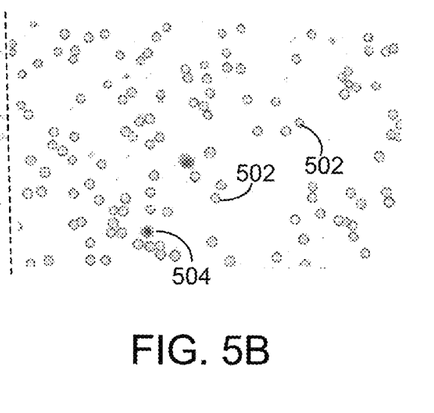
FIG. 5B is an enlarged view of a portion of an image field of a blood sample showing classified cells.
Figure 6:
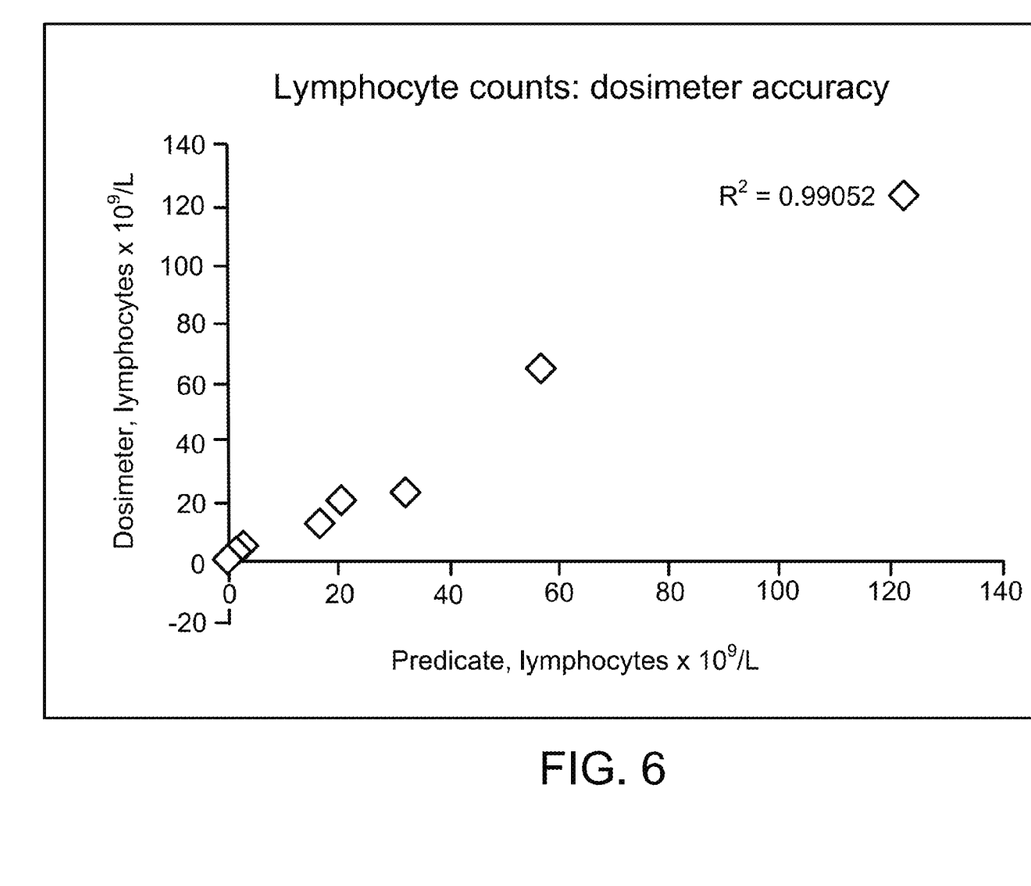
FIG. 6 is a linear regression analysis of lymphocyte counts of blood samples as determined by a dosimeter of this disclosure, plotted against lymphocyte counts of the same blood samples measured by a current hospital standard instrument.

One or more algorithms, e.g., in the form of computer vision software, are then used to analyze the data output (408) from the lensless imaging system. For example, the algorithm(s) identify lymphocytes among the imaged particles in the blood, on the basis of color and size of cell, nuclear shape and size, and/or other parameters. As an example, FIG. 5A shows a portion of an imaged field 500 of a blood sample. FIG. 5B shows erythrocytes 502 and leukocytes 504 that are automatically classified and labeled (with circles) by the software. Absolute lymphocyte count is then determined based on the classified cells, such as those shown in FIG. 5B, which may be corrected based on the volume and dilution of the imaged blood sample, if any. An example showing the accuracy of the lymphocyte counts determined by a dosimeter of this disclosure is shown in FIG. 6. A linear regression analysis of such lymphocyte counts of blood samples as determined by a dosimeter of this disclosure is plotted against lymphocyte counts of the same blood samples measured by a current hospital standard instrument.

If the time from radiation exposure to blood sampling is known, a single lymphocyte count may be used to estimate a depletion rate of lymphocyte, and thus an absorbed radiation dose, assuming pre-exposure count was normal average. In some implementations, the lymphocyte depletion is determined based on the count of lymphocytes with reference to normal count in similar individuals. In an example, the reference normal count can be $2.45 \times 10^9$ cells/L. The reference normal count can be corrected for age, sex, etc. The normal average is generally known. See, for example, The Medical Basis for Radiation Accident Preparedness, K F Hubner, S F Fry, eds, Elsevier North Holland Inc., 1980, 297-310, and Annuals of Internal Medicine, 2004, vol 140: 1037-51.

In some implementations, more accurate estimates can be achieved by obtaining a second blood sample from the same individual after an interval of several hours. In some implementations, even more blood samples can be taken and analyzed. The lymphocyte depletion rate can be calculated based on the following model (see, e.g., "Acute Radiation Syndrome Treatment Guidelines," Radiation injury Treatment Network, September 2010; http://www.ritn.net/WorkArea/DownloadAsset.aspx?id=2147483696, the entire content of which is incorporated here by reference):

$$Lt = 2.45 \times 10^9 / L \times e^{-k(D)t}$$

where Lt equals the lymphocyte count, $2.45 \times 10^9$ cells/L equals a constant representing the consensus mean lymphocyte count in the general population, k(D) equals the lymphocyte depletion rate constant for a specific acute photon dose D, and t equals the time after exposure (days). A calculator for dose estimation by these means is available at the U.S. Department of Health and Human Services' Radiation Emergency Medical Management website, http://www.remm.nlm.gov/ars_wbd.htm#lymphocyte.

In some implementations, the lymphocyte counts can be further corrected based on known variation factors. For example, lymphocytes may not distribute perfectly uniformly within a blood sample, and the non-uniform distribution may lead to a difference between the actual number of lymphocyte and the counts produced by the dosimeter.

Furthermore, the volume of the chamber in the lensless imaging system may also vary from test to test. As a result, the actual volume of a sample being imaged may differ from sample to sample. The variation factors can be statistically determined for correcting the lymphocyte counts.

An example of determining the variation factor originated from the chamber volume variation is explained as follows. The actual volume of the chamber is determined by counting fiduciary beads included with a blood sample at a known concentration for reducing errors due to variations in chamber volume. Based on an assumption of 1,000 beads in the blood sample, the variation in count due to random distribution is 3.3% (1,000 beads, standard deviation of the count=32.85, coefficient of variation (CV)=3.3%). These two independent error sources (from the chamber volume and the bead count) result in a combined error of 8.9%. In some implementations, the surface area of the sensors is increased and the aggregate volume error factor is less than 5%.

In some implementations, the analyzed volume is increased by reloading sample into the chamber after the first data acquisition. The counting statistics for rare cells (or particles) can be improved by introducing a new volume of sample. As the volume loaded (~10 µL or more) is much larger than the volume actually monitored when the chamber top is lowered into place (~0.1 µL), a new volume of sample can be efficiently reloaded by raising and lowering the chamber top a few times to mix the sample before re-lowering the chamber top into its "read" position. The rapid raising and lowering mechanism of the chamber top is a generally useful strategy for improving sampling statistics.

In some implementations, it takes approximately 30 seconds for sample transfer and image acquisition (e.g., steps 404 and 406 of the process 400 shown in FIG. 4), and approximately 120 seconds or less, e.g., less than 30 seconds or less than 15 seconds, for image processing and analysis. Taking subject preparation and device cleaning into account, throughput of each dosimeter can be more than 30 tests per hour.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. Alternatively or in addition, the program instructions can be encoded on an artificially generated propagated signal, e.g., a machine-generated electrical, optical, or electromagnetic signal, that is generated to encode information for transmission to suitable receiver apparatus for execution by a data processing apparatus. The computer storage medium can be a machine-readable storage device, a machine-readable storage substrate, a random or serial access memory device, or a combination of one or more of them.

The term "data processing apparatus" refers to data processing hardware and encompasses all kinds of apparatus, devices, and machines for processing data, including by way of example a programmable digital processor, a digital computer, or multiple digital processors or computers. The apparatus can also be or further include special purpose logic circuitry, e.g., an FPGA (field programmable gate array) or an ASIC (application specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, a module, a software module, a script, or code, can be written in any form of programming language, including compiled or interpreted languages, or declarative or procedural languages, and it can be deployed in any form, including as a stand alone program or as a module, component, subroutine, or other unit suitable for use in a computing environment. A computer program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

The processes and logic flows described in this specification can be performed by one or more programmable computers executing one or more computer programs to perform functions by operating on input data and generating output. The processes and logic flows can also be performed by, and apparatus can also be implemented as, special purpose logic circuitry, e.g., an FPGA (field programmable gate array) or an ASIC (application specific integrated circuit). For a system of one or more computers to be "configured to" perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Computers suitable for the execution of a computer program, by way of example, can be based on general or special purpose microprocessors or both, or any other kind of central processing unit. Generally, a central processing unit will receive instructions and data from a read only memory or a random access memory or both. The essential elements of a computer are a central processing unit for performing or executing instructions and one or more memory devices for storing instructions and data. Generally, a computer will also include, or be operatively coupled to receive data from or transfer data to, or both, one or more mass storage devices for storing data, e.g., magnetic storage, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer readable media suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

Control of the various systems and processes described in this specification, or portions of them, can be implemented in a computer program product that includes instructions that are stored on one or more non-transitory machine-readable storage media, and that are executable on one or more processing devices. The systems described in this specification, or portions of them, can be implemented as an apparatus, method, or electronic system that may include one or more processing devices and memory to store executable instructions to perform the operations described in this specification.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous. In addition to uses in radiation exposure caused by accidents, the dosimeters can also be used in radiation therapies, such as treatment for cancer, and in experimental research.

What is claimed is:

1. An apparatus comprising:
a lensless imaging system comprising
an array of sensors exposed at a common sensor surface, and
a microscopy sample chamber to receive a sample for imaging; and
a processor configured to
receive a microscopy image of at least a part of the sample in the chamber generated by the array of sensors of the lensless imaging system, the at least part of the sample containing blood removed from a subject, the blood having absorbed a dose of radiation before being removed from the subject;
from the received microscopy image determine a count of cells of at least one type in the blood in the at least part of the sample,
determine if the cells of the at least one type are non-uniformly distributed within the part of the sample of the received image; and
correct the count of the cells of the at least one type if the cells of the at least one type are non-uniformly distributed within the part of the sample of the received image.

2. The apparatus of claim 1, wherein the array of sensors is formed in a CMOS chip.

3. The apparatus of claim 1, wherein each sensor of the array of sensors has a size of about 2 µm by 2 µm or smaller.

4. The apparatus of claim 1, wherein the processor is configured to automatically analyze data contained in the image.

5. The apparatus of claim 4, wherein automatically analyzing the data comprises classifying different types of cells in the image.

6. The apparatus of claim 1, wherein the processor is configured to derive the radiation dose the subject has absorbed based on the count.

7. The apparatus of claim 1, wherein the processor is configured to automatically deliver the received image to a machine external to the apparatus for the machine to process information contained in the image and provide information about the radiation dosage.

8. The apparatus of claim 1, comprising a network interface for connecting the apparatus to a network through wire or wireless connections.

9. The apparatus of claim 1, wherein the apparatus comprises a handheld device.

10. The apparatus of claim 1, wherein the sensors comprise digital image sensors capable of lensless optical microscopy.

11. The apparatus of claim 1, comprising a computer-readable storage medium that stores reference hematological bio-dosimetry data for one or more cell types.

12. The apparatus of claim 11, wherein the processor is configured to derive the radiation dosage the subject has absorbed based on comparing a count of one or more cell types to the reference biodosimetry data for the one or more cell types.

13. The apparatus of claim 1, wherein the processor is configured to estimate lymphocyte depletion based on one or more counts of lymphocytes.

14. The apparatus of claim 1, wherein the processor is configured to:
determine a first count of a first type of cells within a first sample received within the chamber at a first time;
determine a second count of the first type of cells within a second sample received within the chamber at a second time after the first time; and
estimate the change in concentration of the first type of cells based on comparing the first count to the second count.

15. The apparatus of claim 1, wherein the processor is configured to correct the count of the cells of the at least one type based on a volume of the sample.

16. The apparatus of claim 1, comprising a sample delivery component for preparing and delivering the sample onto the sensor surface.

17. The apparatus of claim 1, wherein the sample is to contain capillary blood obtained by a pin prick of the subject.

18. The apparatus of claim 1, wherein the sample is to contain microbeads coupled to other molecules to endow the microbeads with binding specificity.

19. The apparatus of claim 18, wherein the microbeads are to comprise microbeads of two or more different sizes.

20. The apparatus of claim 18, wherein the microbeads are to comprise microbeads of two or more different shapes.

21. The apparatus of claim 18, wherein the microbeads are to comprise microbeads that are at least one of transparent, colored, fluorescent, and opaque.

22. The apparatus of claim 1, comprising a mechanism configured to move a first surface of the chamber relative to the sensor surface.

23. The apparatus of claim 22, wherein the mechanism is configured to move the first surface parallel to the-sensor surface during at least part of the motion.

24. The apparatus of claim 22, wherein the mechanism is configured to move the first surface to a designated location toward the sensor surface such that when the first surface is moved to the designated location, the part of the sample that is included in the image includes cells distributed in no more than a monolayer in the sample.

25. The apparatus of claim 1, wherein the sample received on the sensor surface of the chamber comprises one or more of anticoagulant, diluent, stain, antibody, erythrocyte lysing solution, and other reagents.

26. The apparatus of claim 1, wherein the processor is configured to generate the count of the cells of the at least one type based on a volume of diluent within the sample.

27. The apparatus of claim 1, wherein the processor is configured to generate the count of the cells of the at least one type based on detecting one or more surface antigens associated with the cells of the at least one type.

28. The apparatus of claim 1, wherein the array of sensors comprises 1 megapixel or higher sensors.

29. The apparatus of claim 1, wherein the chamber comprises one or more components to mix a volume of the sample received on the sensor surface by raising and lowering a surface of the chamber.

30. The apparatus of claim 1, wherein the chamber has a height to accommodate no more than a monolayer of blood cells in the sample.

31. The apparatus of claim 1 in which the sample is in contact with the sensor surface.

32. The apparatus of claim 1 in which the sample has a predetermined volume.

33. The apparatus of claim 1 in which the cells of the at least one type comprise lymphocytes.

34. The apparatus of claim 1 in which the change in concentration comprises depletion.

35. The apparatus of claim 1 in which the processor is configured to, based on the count, determine a degree of change in concentration of the cells of the at least one type in the blood.

36. The apparatus of claim 35 in which the processor is configured to, based on the degree of change in the concentration of the cells of the at least one type in the blood, display information associated with a radiation dose absorbed by the subject.

37. An apparatus comprising:
a lensless imaging system comprising
an array of sensors exposed at a sensor surface, and
a chamber to receive a sample containing blood having absorbed a dose of radiation before being removed from a subject; and
a processor configured to
receive a microscopy image of at least a part of the sample in the chamber generated by the array of sensors,
from the received microscopy image determine a count of cells of at least one type in the blood in the at least part of the sample, and
correct the count of the cells of the at least one type to account for a non-uniform distribution of the cells within the part of the sample of the received image.

* * * * *